(12) United States Patent
Mazuir et al.

(10) Patent No.: US 7,613,505 B2
(45) Date of Patent: Nov. 3, 2009

(54) DEVICE FOR THE DETECTION AND CHARACTERIZATION OF BIOLOGICAL TISSUE

(75) Inventors: Alain Mazuir, Marseilles (FR); Francis Dieras, Bordeaux (FR)

(73) Assignee: Sopro, La Ciotat (FR)

( * ) Notice: Subject to any disclaimer, the term of this patent is extended or adjusted under 35 U.S.C. 154(b) by 223 days.

(21) Appl. No.: 10/565,589

(22) PCT Filed: Jul. 28, 2004

(86) PCT No.: PCT/FR2004/002026

§ 371 (c)(1),
(2), (4) Date: Mar. 8, 2006

(87) PCT Pub. No.: WO2005/011486

PCT Pub. Date: Feb. 10, 2005

(65) Prior Publication Data

US 2006/0227216 A1  Oct. 12, 2006

(30) Foreign Application Priority Data

Jul. 28, 2003  (FR) .................... 03 09256

(51) Int. Cl.
*A61B 6/00* (2006.01)
(52) U.S. Cl. ...................................... 600/476
(58) Field of Classification Search ............... 607/91; 348/207.99; 600/437, 473, 476
See application file for complete search history.

(56) References Cited

U.S. PATENT DOCUMENTS

| | | | | | |
|---|---|---|---|---|---|
| 5,042,494 | A | * | 8/1991 | Alfano | 600/477 |
| 5,507,287 | A | * | 4/1996 | Palcic et al. | 600/317 |
| 5,880,826 | A | * | 3/1999 | Jung et al. | 356/73 |
| 6,295,322 | B1 | | 9/2001 | Bessler et al. | |
| 6,393,315 | B1 | * | 5/2002 | Aprahamian et al. | 600/476 |
| 6,593,967 | B1 | | 7/2003 | Laroche et al. | |
| 2001/0049473 | A1 | * | 12/2001 | Hayashi | 600/317 |

FOREIGN PATENT DOCUMENTS

FR  2 825 260  12/2002

* cited by examiner

*Primary Examiner*—Eric F Winakur
*Assistant Examiner*—Katherine L Fernandez
(74) *Attorney, Agent, or Firm*—Young & Thompson

(57) ABSTRACT

Method for detection and location of a difference in density and/or structure and/or chemical composition of a biological tissue (7) which is subjected to continuous illumination in a first determined band of frequencies, causing the former to generate a phenomenon of fluorescence, autofluorescence or luminescence in a second band of frequencies. The method includes the following stages: the biological tissue thus illuminated is visually captured by color video elements provided with image sensors with a mosaic of pixels provided with additional color filters; for each image point thus obtained 1) information relating to the energy received by each pixel is collected in order to reconstitute an image of the biological tissue (7), b) amplification occurs for the signal corresponding to the energy received in the second frequency band in order to characterize the biological tissue (7) difference or to cause the image thus obtained to appear.

14 Claims, 1 Drawing Sheet

DEVICE FOR THE DETECTION AND CHARACTERIZATION OF BIOLOGICAL TISSUE

BACKGROUND OF THE INVENTION

1. Field of the Invention

The present invention relates to a method and device for detecting, locating and characterizing differences in density, structure or chemical composition of a biological tissue.

2. Description of the Related Art

In the prior art various methods have been put forward for detecting or evidencing tissue differences of physiological or histological origin, whether pathological or not, using the auto-fluorescence of tissues containing endogenous chromophores or the fluorescence caused by administered dyes or exogenous chromophores.

This made it possible to achieve real time mapping of the fluorescence of living tissues, based on the principle according to which the chromophore content differs depending on whether the observed area is healthy or damaged.

Said method has been used for the direct observation of decay damage on hard tissues such as tooth enamel, or on soft tissues such as the skin or oral mucosa, or via endoscopic route for observing thoracic or gastric endocavity mucosa.

Various methods have also been proposed for detecting and characterizing tissue differences in which the tissues are illuminated by means of a monochromatic light of determined wavelength so as cause this light to feed back radiation by luminescence at a different wavelength.

According to this principle, and as an example, by comparing the intensity of the luminescence emitted by a healthy area of a tooth and a decayed area thereof, using respective measurements in these two specific wavelengths, in particular using a mathematical operation to calculate the difference between these two intensities, it is possible to determine the presence of decay or to evidence tissue difference or surface deterioration in relation to the value obtained.

Said method has also been used for the in vivo detection of inflammatory processes of the pancreas in animal models in which significant tissue discrimination was obtained between healthy tissues and damaged tissues by comparing the spectra and intensity ratios between the blue and red.

In the literature other applications are found, in particular for the in vivo detection of cancers of the tracheal-bronchial structure, for which it was found that the auto-fluorescence of the bronchi is modified when the tissue changes from a dysplastic state to a carcinomatous state. In this case it was found that the lesions led to reduced green fluorescence at around 500 nm and to an increase in the red spectrum band at around 600 nm.

This same principle is also used in ophthalmology to asses the extent of transparency of the lens whose photo-oxidized proteins can be evidenced by fluorescence.

Said applications have recourse to devices using conventional optical means with spectre separation filters.

Said filters have the disadvantage of requiring costly devices that are cumbersome and fragile. The light intensity must be high, which may lead to parasitical fluorescence emissions likely to deteriorate the signal-to-noise ratio and to mask the detection of the relevant signal.

SUMMARY OF THE INVENTION

The purpose of the present invention is to propose a method and device with which it is possible to ensure the detection, locating and characterization of structural or other differences of a biological tissue, this device being of simple design, low cost, easy to use and able to eliminate the different artefacts related to various unknown factors which may act on the tissue surface and disturb measurements.

The subject-matter of the invention is therefore a method for detecting and locating the difference in density and/or structure and/or chemical composition of a biological tissue that is subjected to continuous illumination in a first determined band of frequencies, able to cause the tissue to generate a phenomenon of fluorescence, auto-fluorescence or luminescence in a second band of frequencies, characterized in that it comprises the following steps:

capturing an image of the biological tissue illuminated in this way using colour video means provided with image sensors with a mosaic of pixels having complementary colour filters, for each point of the image so obtained:

a) collecting data related to the energy received by each pixel, so as to reconstitute the image of the biological tissue, b) amplifying the signal corresponding to the energy received in the second band of frequencies so as to characterize or cause to appear said difference of the biological tissue in the image obtained.

According to the invention, the data collected in the second band of frequencies may be processed so as to characterize the structure difference obtained in a colour other than the colour naturally corresponding to this second zone of frequencies.

A further subject of the present invention is a device for detecting and locating the difference in density and/or structure and/or chemical composition of a biological tissue, characterized in that it comprises:

means able to continuously illuminate the biological tissue with a light located in a first determined band of frequencies, so as to cause the tissue to generate a phenomenon of fluorescence in a second band of frequencies, colour video means provided with image sensors with a mosaic of pixels provided with complementary colour filters, capture and calculation means which, for each image point so obtained, are able to collect data related to the energy received by each pixel, so as to reconstitute the image of the biological tissue, means for amplifying the signal corresponding to the energy received in the second band of frequencies, so as to characterize or cause to appear the said difference of the biological tissue in the image obtained.

This device may also comprise means for processing the data collected in the second band of frequencies, so as to characterize the structure difference obtained in a colour other than the colour naturally corresponding to this second zone of frequencies.

A further subject of the present invention is a method for detecting and locating the difference in density and/or structure and/or chemical composition of a biological tissue subjected to continuous illumination in a first determined band of frequencies, able to cause the tissue to generate a phenomenon of fluorescence, auto-fluorescence or luminescence in a second band of frequencies, characterized in that it comprises the steps consisting of:

capturing an image of the biological tissue illuminated in this way, using image capturing means consisting of monochrome image sensors, namely a luminance sensor and at least one sensor provided with a filter of the colour corresponding to the colour of the fluorescence emitted during detection of a difference it is desired to evidence, for each point of the image obtained:
- a) collecting data related to the energy received by each pixel, so as to reconstitute the image of the biological tissue,
- b) amplifying the signal corresponding to the energy received in the second band of frequencies so as to characterize or cause to appear the said difference of the biological tissue in the image obtained.

A further subject of the present invention is a device for detecting and locating the difference in density and/or structure and/or chemical composition of a biological tissue, characterized in that it comprises:

- means able to continuously illuminate the biological tissue with a light located in a first determined band of frequencies so as to cause the tissue to generate a phenomenon of fluorescence in a second band of frequencies,
- image-capturing means consisting of monochrome image sensors, namely a luminance sensor and at least one sensor provided with a filter of the colour corresponding to the colour of the fluorescence emitted during detection of a difference to be detected,
- capture and calculation means which, for each point of the image so obtained, are able to collect data related to the energy received by each pixel so as to reconstitute the image of the biological tissue,
- means for amplifying the signal corresponding to the energy received in the second band of frequencies so as to characterize or to cause to appear the said difference of the biological tissue in the image obtained.

The present invention is of particular interest in that, unlike prior art devices, it does not have recourse to a monochrome light source, which enables it firstly to use a greater part of the energy supplied by the light source, and secondly by using a band of radiation located in the visible range, to provide an image of the tissues being examined (in dentistry an image of the tooth or, in another fields, an image of the mucosa, skin, eye, etc . . . ).

In one embodiment of the invention, and concerning for example the case of hard tissue observation such as tooth enamel, in which the second band of frequencies is centred on a primary colour (red in this example), the CCD sensors of the video colour means are provided at each of the pixels with filters whose colour is preferably that of the complementary colours, namely yellow, magenta and cyan. The use of said complementary filters is of interest in that firstly the range of reaction of these filters, and hence the sensitivity of the sensors, is greater than those of the primary colours, and secondly it thereby becomes possible to act on two signals, namely those of the complementary colours associated with each of the primary colours, instead of only being able to act on a single signal namely the signal associated with the primary colours, thereby making it possible to ensure improved management of the filtering used.

BRIEF DESCRIPTION OF THE DRAWING FIGURES

An embodiment of the present invention is described below as a non-restrictive example with reference to the appended drawing in which.

DETAILED DESCRIPTION OF THE PREFERRED EMBODIMENTS

Figure 1:
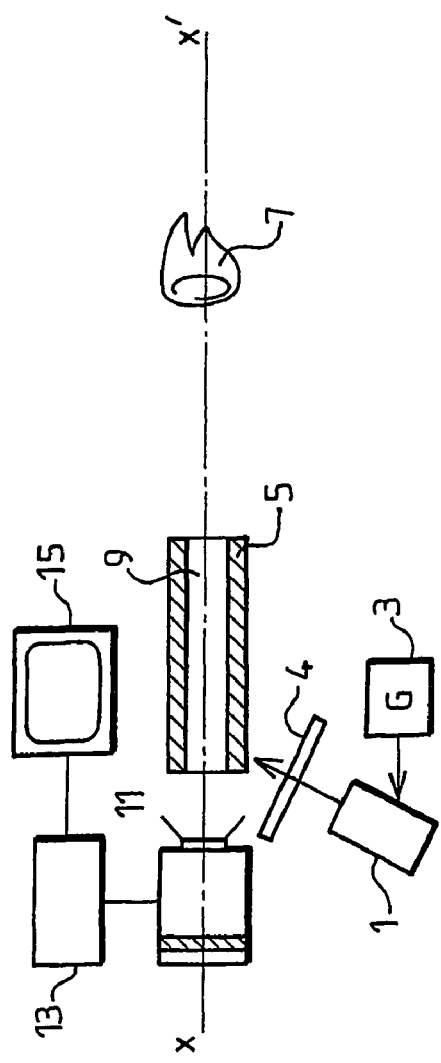
FIG. 1 is a schematic view of the inventive device for detecting, locating and characterizing the structural difference of a biological tissue.

The inventive device shown FIG. 1 consists of a xenon lamp 1 supplied by a current generator 3. The light which is non-monochrome and supplied by lamp 1 is filtered on leaving the lamp by a filter 4 enabling the maintaining of a radiation band extending from the ultraviolet to the near visible. These light radiations pass through a waveguide tube 5 and continuously illuminate a biological tissue, in this case a patient's tooth 7. The waveguide tube 5 is crossed by a central, longitudinal channel of axis xx' through which a colour video camera 11 is able to film the tooth 7.

The camera 11 is connected to means for processing the signals 13, these means being connected to video display means 15.

Figure 2:
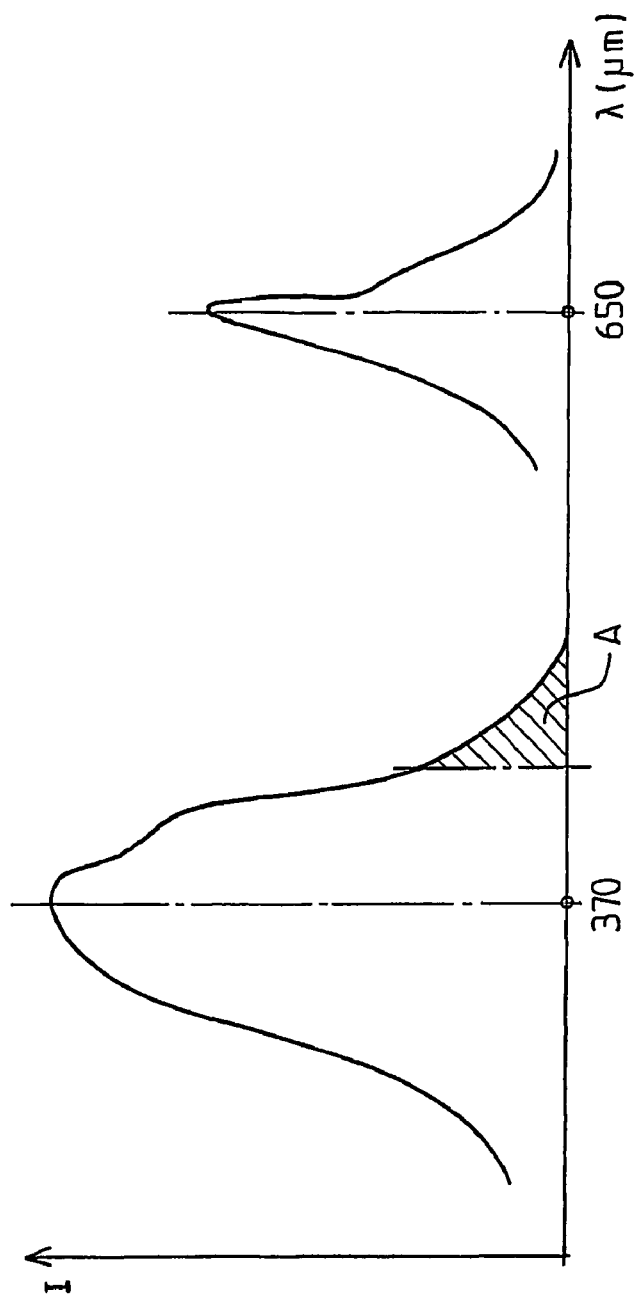
FIG. 2 is a schematic view showing the wavelength ranges to which recourse is made for the clinical application of the invention to the area of dentistry.

The filter 4, in this embodiment, is able to allow a wavelength band to pass that is centred at around 370 nm, part of this band of frequencies, as is shown FIG. 2 comprising a part A located in the visible range.

It is known that under the effect of this illumination the mineral constituent of the tooth, namely the enamel, produces fluorescence radiation located in the green and blue range.

Also, it has been found that the tooth enamel parts which have undergone the onset of partial deterioration on account of tooth decay, emit fluorescence radiation in the 650 nm range, in other words red radiation.

According to the invention, using a colour video camera 11, an image is recorded which is the resultant of several spectral bands, namely:

- an image of the tooth resulting from the illumination produced on the tooth by the visible part of the illumination spectrum,
- an image of the tooth derived from the fluorescence of its enamel generated by its illumination in the ultraviolet range produced by the illumination spectrum,
- a fluorescence image (in the red range i.e. at around 650 nm) emitted by the deteriorated zones of the tooth enamel resulting from decay.

According to the invention the fluorescence signal, generated in the red (at around 650 nm) by the deteriorated parts of the tooth, is amplified. For this purpose the pixels of the CCD sensors are preferably equipped with filters of complementary colours, namely yellow, magenta and cyan to which a green filter is added. Under these conditions it will be understood that a pixel provided with a yellow filter for example will allow the red rays and green rays to pass if said pixel receives light energy. Once this pixel receives light energy it needs to be determined if this light is red radiation, in which case it must be amplified, or on the contrary if it is green radiation in which case it will not be amplified. For this purpose the neighbouring pixel is consulted which has a green filter, and if it is saturated this will mean that the radiation is entirely green and that therefore there is no red radiation to be amplified for this pixel. In the reverse case, it will be red radiation which will lead to amplification.

The process is continued from pixel to pixel for all the pixels of the CCD sensor. This operating mode will translate as display on the video monitor 15 firstly of the image of the tooth (derived, as described above, firstly from its illumination in visible light and secondly from fluorescence of the enamel produced in the blue/green wavelength range), and secondly of the image in red superimposed upon it of the detected decay.

It is evidently possible according to the invention, if need be, to subsequently transform the detected red radiation into display radiations of any other more suitable colour.

With the present invention, to facilitate detection of the deteriorated area of the tooth, it is also possible to eliminate parasite fluorescence of closely similar colours from the display, caused by other parameters such as scale or dental plaque for example or fillings from prior treatments, or any other biological element to contribute towards the desired diagnosis.

It was experimentally ascertained that, by adding radiations to the illumination spectrum that are located in a wavelength range in the order of 400 nm, the produced fluorescence spectrum is modified by shifting the fluorescence band of parasite fluorescence.

By modifying the emission spectrum it is evidently possible to eliminate other phenomena of parasite fluorescence which may disturb measurement and are possibly due to the presence of scale or dental plaque on the tooth enamel.

It is also possible according to the invention to have recourse to monochrome image sensors, in particular of CCD type. The image capturing means would then consist firstly of a first luminance sensor and secondly of a sensor provided with a filter of the colour corresponding to the colour of the fluorescence emitted during detection of the difference it is sought to detect. For example for detecting tooth caries, this filter will have a colour which allows a radiation of 650 nm to pass, and when detecting dysplastic or carcinomatous tissue it will have a colour which allows radiation of 500 nm to pass. Evidently, in this case the inventive device will only be able to detect anomalies of a single type. It would then be possible evidently to provide other monochrome sensors equipped with other filters, each allowing access to an additional application.

In one particular embodiment of the invention, the camera 11 may be provided with means enabling it to operate either under fluorescence detection mode or under visualization mode of the area being examined to produce a conventional video image. For this purpose the lens must be equipped with a filter corresponding to attenuation of the emitted light. The hand-piece of the camera may be provided with a switch enabling use of the dedicated filter when in fluorescence mode or its deactivation for conventional video imaging. In fluorescence mode it will also be possible to place a colour filter in front of the lens to improve contrast.

Although the implementation of the present invention has chiefly been described with regard to applications lying mainly in the dental domain, it may also be applied to the detection and locating of tissue deteriorations such as those of bronchial mucosa whose auto-fluorescence in the green (at around 500 nm) is reduced and is increased in the red at around 600 nm.

Similarly, recourse could be made to sensors other than CCD sensors, CMOS sensors in particular.

It is also possible to detect and locate tissue lesions such as pancreas lesions which, when illuminated in a frequency band centred on radiation of wavelength 400 nm, generate a significant increase in red fluorescence (630 nm).

The invention claimed is:

1. A method for detecting and locating the difference in density and/or structure and/or chemical composition of a biological tissue which is subjected to continuous illumination in a first determined band of frequencies, able to cause the tissue to generate a phenomenon of fluorescence, autofluorescence or luminescence in a second band of frequencies, comprising:
   capturing an image of the biological tissue illuminated in this way, using colour video means provided with image sensors with a mosaic of pixels provided with filters of complementary colours, the filters having a greater range of reaction compared to filters of primary colours, for each point of the image so obtained:
   a) collecting data related to the energy received by each pixel, so as to reconstitute the image of the biological tissue, and
   b) amplifying, pixel by pixel, the signal corresponding to the energy received in the second band of frequencies so as to characterize the said difference of the biological tissue in the image obtained, by acting on signals as received by at least two neighbouring pixels provided with filters of different colours, an amount of amplification of the signal corresponding to the energy received in the second band of frequencies by said at least two neighbouring pixels.

2. The method as claimed in claim 1, wherein the data collected in the second band of frequencies is processed so as to characterize the structure difference obtained in a colour other than the colour naturally corresponding to this second zone of frequencies.

3. The method as claimed in claim 2, wherein radiations are added to the band of frequencies of the illumination spectrum that are able to modify the fluorescence spectrum to shift the fluorescence band of parasite fluorescence.

4. The method as claimed in claim 1, wherein radiations are added to a band of frequencies of the illumination spectrum that are able to modify the fluorescence spectrum to shift a fluorescence band of parasite fluorescence.

5. The method as claimed in claim 1, wherein said complementary colours are cyan, magenta and yellow.

6. The method as claimed in claim 1, wherein said mosaic of pixels is further provided with a green filter.

7. The method as claimed in claim 6, wherein said tissue is a tooth and the fluorescence of deteriorated parts being in the red, for each point of the image, said amplification is realized by acting on signals as received by at least two corresponding neighbouring pixels provided with filters of different colours, said amplification comprising amplifying the energy received by a corresponding yellow pixel when said corresponding neighbouring pixels provided with filters of yellow and green are such that the yellow pixel receives energy while the green pixel does not receive energy, and in not amplifying the energy received by the corresponding yellow pixel when said corresponding neighbouring pixels provided with filters of yellow and green are such that the yellow pixel receives energy while the green pixel is saturated.

8. The method as claimed in claim 1, wherein said first band of frequencies includes a visible part, for each point of the image, said data related to the energy received by each pixel collected so as to reconstitute the image of the biological tissue, are derived from illumination in visible light and from fluorescence produced by said tissue.

9. The method as claimed in claim 1, wherein while translating data for display of each point of the image on a RGB video monitor, said amplifying is realized by providing each red, blue, or green components of at least one point of the image, in addition with data collected so as to reconstitute the image of the biological tissue with a sum of amplified energy as received by at least two neighbouring pixels provided with filters of different colours.

10. The method as claimed in claim 9, wherein said tissue is a tooth and the fluorescence of deteriorated parts being in the red, for each point of the image, said amplification is realized by acting on signals as received by at least two corresponding neighbouring pixels provided with filters of different colours, said amplification comprising amplifying the energy received by a corresponding yellow pixel when said corresponding neighbouring pixels provided with filters of yellow and green are such that the yellow pixel receives energy while the green pixel does not receive energy, and in not amplifying the energy received by the corresponding yellow pixel when said corresponding neighbouring pixels provided with filters of yellow and green are such that the yellow pixel receives energy while the green pixel is saturated.

11. The method as claimed in claim 1, wherein the action on signals as received by at least two neighbouring pixels provided with filters of different colours is realized with consultation of the energy received on another neighbouring pixel.

12. A device for detecting and locating the difference in density and/or structure and/or chemical composition of a biological tissue, comprising:
  means able to illuminate the biological tissue continuously with a light located in a first determined band of frequencies, so as to cause the tissue to generate a phenomenon of fluorescence in a second band of frequencies,
  colour video means provided with image sensors with a mosaic of pixels provided with filters of complementary colours, the filters having a greater range of reaction compared to filters of primary colours,
  capture and calculation means which, for each point of the image so obtained, are able to collect data related to the energy received by each pixel so as to reconstitute the image of the biological tissue, and
  means for amplifying, pixel by pixel, the signal corresponding to the energy received in the second band of frequencies so as to characterize said difference of the biological tissue in the image obtained, by acting on at least two neighbouring signals as received by at least two pixels provided with filters of different colours, an amount of amplification of the signal corresponding to the energy received in the second band of frequencies by said at least two neighbouring pixels.

13. The device as claimed in claim 12, wherein the device further comprises processing means to process data collected in the second band of frequencies, so as to characterize the structure difference obtained in a colour other than the colour naturally corresponding to this second zone of frequencies.

14. The device as claimed in claim 12, wherein the act on signals as received by at least two neighbouring pixels provided with filters of different colours is realized with consultation of the energy received on another neighbouring pixel.

* * * * *

UNITED STATES PATENT AND TRADEMARK OFFICE
CERTIFICATE OF CORRECTION

PATENT NO.       : 7,613,505 B2                                                Page 1 of 1
APPLICATION NO. : 10/565589
DATED            : November 3, 2009
INVENTOR(S)      : Mazuir et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this

Nineteenth Day of October, 2010

David J. Kappos
*Director of the United States Patent and Trademark Office*